United States Patent
Brem et al.

(10) Patent No.: US 6,482,810 B1
(45) Date of Patent: Nov. 19, 2002

(54) ANTIBIOTIC COMPOSITION FOR INHIBITION OF ANGIOGENESIS

(76) Inventors: Henry Brem, 11201 Five Springs Rd., Lutherville, MD (US) 21093; Rafael J. Tamargo, 2306 Pennyroyal Ter., Baltimore, MD (US) 21209; Robert A. Bok, #158, 3121 Chowen Ave. South, Minneapolis, MN (US) 55416

( * ) Notice: Subject to any disclaimer, the term of this patent is extended or adjusted under 35 U.S.C. 154(b) by 0 days.

(21) Appl. No.: 08/227,100

(22) Filed: Apr. 13, 1994

Related U.S. Application Data

(63) Continuation of application No. 07/641,498, filed on Jan. 15, 1991, now abandoned.

(51) Int. Cl.⁷ .............................................. A61K 31/65
(52) U.S. Cl. ..................................................... 514/152
(58) Field of Search .......................................... 514/152

(56) References Cited

U.S. PATENT DOCUMENTS 3,326,761 A * 6/1967 Kent ............................ 167/78

OTHER PUBLICATIONS

Kroon et al, Cancer Letters, vol. 25 1984 pp. 33–40.*
Kroon et al, Drugs Expl. clim. Res, vol. 11, 1984, pp. 759–766.*

* cited by examiner

Primary Examiner—Russell Travers
(74) Attorney, Agent, or Firm—Holland & Knight LLP

(57) ABSTRACT

Pharmaceutical compositions for delivering an effective dose of an angiogenesis inhibitor consisting of a tetracycline or tetracycline such as minocycline. The effective dosage for inhibition of angiogenesis based on in vitro testing is between one and 500 micromolar. The compositions are delivered topically, locally or systemically using implants or injection. The composition is extremely selective for growth of endothelial cells, inhibiting growth, but is not cytotoxic at the effective dosages.

13 Claims, 1 Drawing Sheet

ANTIBIOTIC COMPOSITION FOR INHIBITION OF ANGIOGENESIS

This is a continuation of application Ser. No. 07/641,498 now abandonded filed on Jan. 15, 1991.

The U.S. government has rights in this invention by virtue of a grant from the National Institutes of Health, grant number NSO1058-01.

BACKGROUND OF THE INVENTION

This invention is in the field of angiogenesis inhibitors, in particular antibiotics that inhibit angiogenesis.

Angiogenesis, the proliferation and migration of endothelial cells that result in the formation of new blood vessels, is an essential event in a wide variety of normal and pathological processes. For example, angiogenesis plays a critical role in embryogenesis, wound healing, psoriasis, diabetic retinopathy, and tumor formation, as reported by Folkman, J. *Angiogenesis and its inhibitors*. In: V. T. DeVita, S. Hellman and S. A. Rosenberg (eds.). *Important Advances in Oncology*, pp. 42–62, (J. B. Lippincott Co., Philadelphia, 1985); Brem, H., et al., *Brain tumor angiogenesis*. In: P. L. Kornblith and M. D. Walker (eds.), *Advances in Neuro-Oncology*, pp. 89–101. (Future Publishing Co., Mount Kisco, N.Y. 1988); Folkman, J. *Tumor angiogenesis: therapeutic implications. N. Engl. J. Med.*, 285; 1182–1186 (1971); and Folkman, J. *Successful treatment of an angiogenic disease. N. Engl. J. Med.*, 320: 1211–1212 (1989).

Identification of several agents that inhibit tumor angiogenesis has provided a conceptual framework for the understanding of angiogenesis in general. The inhibition of angiogenesis by certain steroids and heparin derivatives, reported by Folkman, J., et al., *Science* 221: 719. (1983); and Murray, J. B., et al., *Purification and partial amino acid sequence of a bovine cartilage-derived collagenase inhibitor. J. Biol. Chem.*, 261: 4154–4159 (1986); led to studies elucidating the crucial role of remodeling of the extracellular matrix in angiogenesis. These agents apparently prevent angiogenesis by specifically disrupting the deposition and cross-linking of collagen, as reported by Ingber, D., and Folkman, J. *Inhibition of angiogenesis through modulation of collagen metabolism. Lab. Invest.*, 59: 44–51 (1989).

The original description of angiogenesis inhibition in the presence of cartilage, reported by Brem, H., et al., *J. Exp. Med.* 141: 427–439 (1975); Brem, H., et al., *Extracellular Matrices Influences on Gene Expression* pp. 767–772 (Academic Press, NY 1975); and Langer, R., et al., *Science* 70–72 (1976); led to the isolation and purification from bovine cartilage of a protein fraction that not only inhibited angiogenesis but inhibited protease activity, described by Murray, J. B., et al., *J. Biol. Chem.* 261: 4154–4159 (1986). Subsequently, an extract derived from the vitreous of rabbits was shown to inhibit tumor angiogenesis by Brem, S., et al., *Am. J. Ophthal.* 84: 323–328 (1977). The demonstration that heparin alone enhanced the angiogenesis response buttressed the hypothesis that heparin produced by mast cells that had migrated to the tumor site facilitated the development of new capillaries, as reported by Kessler, D. A., et al., *Int. J. Cancer* 18:703–709 (1976).

Recent studies on inhibition of angiogenesis have highlighted the importance of enzyme mediated remodeling of the extracellular matrix in capillary growth and proliferation (Folkman, J., et al., *Science* 221: 719–725 (1983),.; Ingber, D., et al. *Lab. Invest.* 59: 44–51 (1989); Folkman, J., et al., *Science* 243: 1490–1493 (1989); Krum, R., et al., *Science* 230: 1375–1378 (1985); Ingber, D., et al., *Endocrinol.* 119: 1768–1775 (1986); and Ingber, D., et al., *J. Cell. Biol.* 109: 317–330 (1989)). It has been suggested Ingber, D., et al., *Lab. Invest.* (1989) and *Endocrinol.* (1986) that the steroid-heparin combination is involved in the dissolution of the capillary basement membrane by inhibiting the deposition or cross-linking of collagen. The isolation of a collagenase inhibitor from cartilage, the first source of an angiogenesis inhibitor, was of interest since it suggested that angiogenesis may be inhibited not only by disrupting collagen deposition, but also by interrupting collagen breakdown. It is therefore possible that a combination of agents that interfere with both the anabolic and catabolic phases of collagen metabolism will prove even more effective in halting tumor angiogenesis.

A number of investigators have reported that extracts of cartilage, one of the few avascular tissues in the body, can inhibit angiogenesis: Eisenstein, et al., *Am. J. Pathol.* 81, 1–9 (1987); Pauli, et al., *J. Natl. Cancer Inst.* 67,55–74 (1981); Brem and Folkman, *J. Exp. Med.* 141, 427–439 (1975); Langer, et al., *Science* 193, 70–72 (1976); Langer, et al., *Proc. Natl. Acad. Sci. USA* 77, 431–435 (1980); and Lee and Langer, *Science* 221, 1185–1187 (1983). Langer, et al., showed that cartilage extracts containing a collagenase inhibitor retard tumor-induced and inflammatory-induced neovascularization in the cornea and conjunctiva, when delivered by either infusion or sustained release from a polymeric implant.

Although extracts from several different tissue sources have been shown to contain anti-angiogenic activity, as reviewed by D'Amore, *Prop. Clin. Biol. Res.* 221, 269–283 (1986), and several molecules have been found which inhibit different aspects of angiogenesis, such as cell proliferation or cell migration, no single tissue-derived macromolecule capable of inhibiting angiogenesis has been identified in the prior art. However, other inhibitors of collagenase are known that do not inhibit angiogenesis, including $\alpha_2$-macroglobulin and tissue inhibitor or metalloproteinase (TIMP). TIMP inhibits capillary endothelial cell proliferation but not angiogenesis. Protamine inhibits blood vessel ingrowth but not proliferation of capillary endothelial cells.

The potential therapeutic benefit that an effective, economic, well characterized inhibitor of angiogenesis might have in controlling diseases in which neovascularization plays a critical role has prompted a long term search for angiogenesis inhibitors. There are many advantages to having such an inhibitor that can be prepared by simple organic synthesis, rather than by cloning and expression of a protein, or synthesis of a long polypeptide. An inhibitor of angiogenesis could have an important therapeutic role in relieving the course of these disorders, as well as provide a valuable means of studying their etiology.

It is therefore an object of the present invention to provide a pharmaceutical composition, and method of use thereof, for the treatment of diseases involving abnormal angiogenesis.

It is another object of the present invention to provide topical and controlled release pharmaceutical compositions, and methods of use thereof, for inhibition of angiogenesis.

It is still another object of the present invention to provide an economical, well characterized, composition for inhibition of angiogenesis.

SUMMARY OF THE INVENTION

An antibiotic composition that is an effective inhibitor of angiogenesis has been developed. The preferred antibiotic is minocycline, although other tetracycline-like antibiotics that inhibit collagenase are also effective.

The effective dosage for inhibition of angiogenesis in vivo is extrapolated from in vitro and in vivo inhibition assays. Effective dosages range from approximately one micromolar to 500 micromolar. The dosage range is much higher than the dosage used for inhibition of bacterial growth. The effective dosage is somewhat dependent on the method and means of delivery. For example, in some applications, as in the treatment of psoriasis or diabetic retinopathy, the inhibitor is delivered in a topical carrier. In other applications, as in the treatment of solid tumors, the inhibitor can be delivered by means of a biocompatible, biodegradable or non-degradable, polymeric implant, systemically, or by local infusion.

Effectiveness was demonstrated by incorporating minocycline into controlled release polymers and testing in the rabbit cornea against neovascularization in the presence of the VX2 carcinoma. Inhibition by minocycline was shown to be comparable to that of the combination of heparin and cortisone, a potent inhibitor of angiogenesis. Minocycline decreased tumor-induced angiogenesis by a factor of 4.5, 4.4 and 2.9 at 7, 14 and 21 days, respectively. At the end of the study, none of the corneas with minocycline had such vascular masses, in contrast to the corneas with empty polymers, which had large, invasive, exophytic tumors. Further studies demonstrate the selectivity of the compound for endothelial cells.

BRIEF DESCRIPTION OF THE DRAWINGS

FIG. 2A, 2B, and 2C are graphs demonstrating the selective inhibition of endothelial cell growth by minocycline: FIG. 2A graphs cells (% of control) for three cell types: pericytes (empty squares), astracytes (dark circles), and endothelial cells (dark squares) versus concentration of minocycline (micromolar). FIG. 2B graphs DNA synthesis (cpm $^3$H-thymidine/microgram protein, % of control) versus concentration of minocycline (micromolar). FIG. 2CB graphs doubling time (% control) for paraaortic endothelial cells (empty squares) and bovine retinal endothelial cells (dark diamonds) versus concentration of minocycline (micromolar).

DETAILED DESCRIPTION OF THE INVENTION

Figure 1:
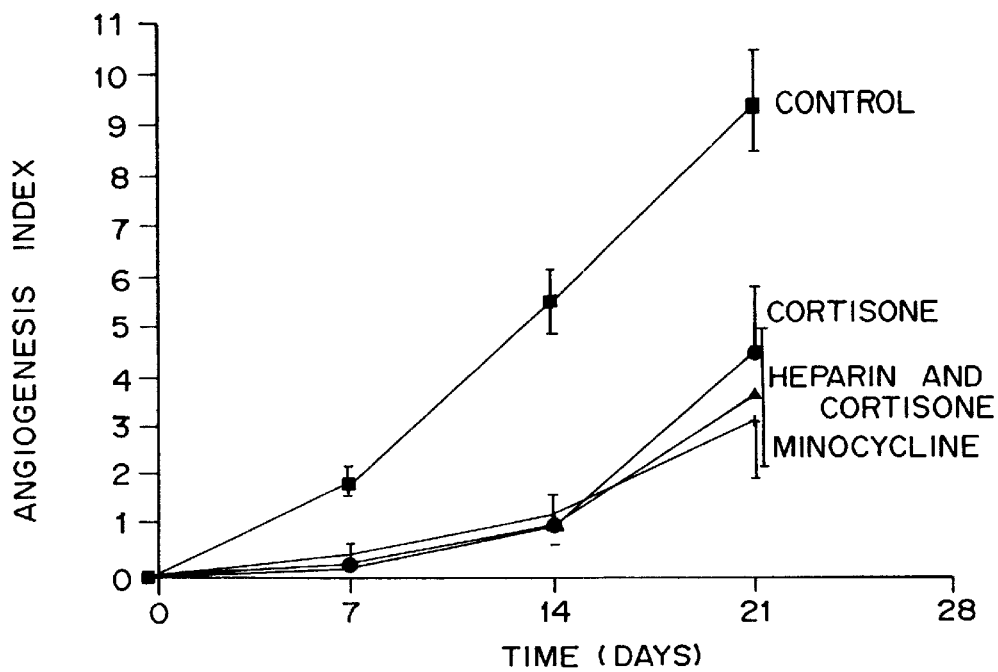
FIG. 1 is a graph comparing the extent of inhibition of angiogenesis (Angiogenesis index) in rabbit cornea over time (days) for the control (squares); cortisone (circles); heparin in combination with cortisone (triangles); and minocycline (+).

Antibiotics effective as inhibitors of angiogenesis have been discovered. The antibiotics are tetracyclines inhibiting collagenase. The preferred antibiotic is minocycline, a semi-synthetic tetracycline antimicrobial with anticollagenase properties.

Minocycline, a semisynthetic tetracycline antimicrobial, described by Martell, M. J., and Boothe, J. H. in *J. Med. Chem.*, 10: 44–46 (1967), and Zbinovsky, Y., and Chrikian, G. P. *Minocycline.* In: K. Florey (ed.), *Analytical Profiles of Drug Substances,* pp. 323–339 (Academic Press, NY 1977), the teachings of which are incorporated herein, has anticollagenase properties, as reported by Golub. L. M., et al., *J. Periodontal Res.*, 18: 516–526 (1983); Golub, L. M., et al., *J. Periodontal Res.* 19: 651–655 (1984); Golub, L. M., et al., *J. Periodontal Res.* 20: 12–23 (1985); and Golub, L. M., et al., *J. Dent. Res.*, 66: 1310–1314 (1987). Minocycline, first described in 1967, is derived from the naturally produced parent compounds chlortetracycline and oxytetracycline. The tetracyclines are effective against a broad range of pathogens, as reported by Laskin, A. J. *Tetracyclines,* In: D. Gotlieb and P. D. Shaw (eds.), *Antibiotics,* pp. 331–359 (Springer-Verlag, N.Y. 1967). They bind to the bacterial 30S ribosome, block access of the aminoacyl tRNA to the binding site on the mRNA-ribosome complex, and thereby inhibit protein synthesis by preventing the addition of amino acids to the growing peptide chain. The tetracyclines usually spare protein synthesis in mammalian cells since these cells lack the active transport system found in bacteria.

Minocycline inhibits collagenase activity directly by a mechanism unrelated to its antimicrobial properties. Minocycline has been shown to inhibit collagenolysis and cytolysis induced by melanoma-produced metalloproteases in vitro, as reported by Zuker, S., *J. Natl. Cancer Inst.* 75:517–525 (1985), and the collagenase activity in the synovial fluid of patients with rheumatoid arthritis, as reported by Greenwald, R. A., et al., *J. Rheumatol.* 14:28–32 (1987). The mode of action of minocycline on collagenase is not well understood.

Minocycline is ideally suited for studying inhibition of angiogenesis since it is readily available commercially, is innocuous to mammalian cells, and has been in clinical use for several years. One of the appealing features of anticollagenase agents as potential antineoplastic agents is that they could be used to inhibit pathological collagenolytic processes, while leaving physiologically necessary proteolytic processes unaffected. Specific collagenase inhibitors with low systemic toxicity can be very useful as modulators of tumor growth.

The effective dosage range is between one and 500 micromolar, based on in vitro studies. The dosage optimum is 50 micromolar. No cytotoxicity is observed within this dosage range. The effective dosage range is much higher than the dosage range used for inhibition of bacteria, which is in the range of less than one micromolar.

Pharmaceutical compositions are prepared using the antibiotic as the active agent to inhibit angiogenesis based on the specific application. Application is either topical, localized, or systemic. Any of these compositions may also include preservatives, antioxidants, antibiotics, immunosuppressants, and other biologically or pharmaceutically effective agents which do not exert a detrimental effect on the antibiotic or cells. For treatment of tumors, the composition may include a cytotoxic agent which selectively kills the faster replicating tumor cells, many of which are known and clinically in use.

For topical application, the antibiotic is combined with a carrier so that an effective dosage is delivered, based on the desired activity, at the site of application. The topical composition can be applied to the skin for treatment of diseases such as psoriasis. The carrier may be in the form of an ointment, cream, gel, paste, foam, aerosol, suppository, pad or gelled stick. A topical composition for treatment of eye disorders consists of an effective amount of antibiotic in a ophthalmically acceptable excipient such as buffered saline, mineral oil, vegetable oils such as corn or arachis oil, petroleum jelly, Miglyol 182, alcohol solutions, or liposomes or liposome-like products.

Compositions for local or systemic administration, for example, into a tumor, will generally include an inert diluent. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

For directed internal topical applications, for example for treatment of hemorrhoids, the composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

In a preferred form, the composition is administered in combination with a biocompatible polymeric implant which releases the antibiotic over a controlled period of time at a selected site. Examples of preferred biodegradable polymeric materials include polyanhydrides, polyorthoesters, polyglycolic acid, polylactic acid, polyethylene vinyl acetate, and copolymers and blends thereof. Examples of preferred non-biodegradable polymeric materials include ethylene vinyl acetate copolymers.

The composition can be administered systemically using any of several routes, including intravenous, intracranial, subcutaneous, orally, or by means of a depo. The composition can be administered by means of an infusion pump, for example, of the type used for delivering insulin or chemotherapy to specific organs or tumors, or by injection.

EXAMPLE 1

Demonstration of Effectiveness of Minocycline in Inhibiting Angiogenesis.

To test for inhibition of angiogenesis, compounds were impregnated into controlled release polymers, and assessed in the rabbit cornea, which allows direct, quantitative observation of neovascularization, as follows.

Animals. New Zealand White rabbits weighing about 1.5–2.5 kg were obtained from Bunnyville Farm (Littlestown, Pa.), kept in standard animal facilities, one animal per cage, and given free access to food and water.

Anesthesia. For the corneal implantations, subsequent stereomicroscopic examinations, and serial transplantation of the VX2 tumor in the thigh, the animals were anesthetized with a mixture of xylazine, 15–17 mg/kg, and ketamine, 15–17 mg/kg, injected i.m.

VX2 Rabbit Carcinoma. The VX2 carcinoma, described by Kidd, J. G., and Rous, P. A. *J. Exp. Med.* 71: 813–838 (1940), a serially transplantable tumor syngeneic to the New Zealand White rabbit, was propagated by serial transplantation in the flank of New Zealand White rabbits.

Test Substances and Polymer Preparation. Ethylene-vinyl acetate copolymer (40% vinyl acetate by weight, Elvax 40P) was obtained from the DuPont Co., Wilmington, Del., as used as described by Langer, R., and Folkman, J. *Nature* (Lond.) 263: 797–800 (1976). The polymer was washed extensively in absolute ethyl alcohol, with total volume changes every 24 hours, to extract the inflammatory antioxidant butylhydroxytoluene. The presence of butylhydroxytoluene in the wash was monitored spectrophotometrically at 230 nm, and the washes were continued until the absorbance fell below 0.03 unit. The polymers were then dried in a vacuum desiccator for 5 days.

The agents to be tested for angiogenesis inhibition were incorporated into the ethylene-vinyl acetate copolymer (EVAc) matrix by modification of the fabrication procedure described by Rhine, W. D., et al., *J. Pharm. Sci.,* 69: 265–270 (1980). Minocycline and heparin crystals were ground to a fine powder and sieved through a 200 mesh (74 $\mu$m) screen in a Collector tissue sieve (Belleo Glass, Inc., Vineland, N.J.), to obtain a uniform sample consisting of particles less than 75 $\mu$m in diameter. The final concentrations (w/w) of the angiogenesis inhibitors in the polymers were: (a) minocycline hydrochloride (Sigma Chemical Co., St. Louis, Mo.), 10 and 20%; (b) cortisone acetate (Sigma Chemical Co.), 7.5 and 27%; (c) and heparin (Hepar Inc., Franklin, Ohio) and cortisone acetate, 15 and 30% combined loading, with a fixed 1:8 heparin:cortisone ratio. No significant differences were observed in the degree of angiogenesis inhibition between the two loading levels for each drug.

Rabbit Cornea Angiogenesis Assay. The inhibition of angiogenesis was determined by assaying the degree of angiogenesis in the rabbit cornea in the presence of specified inhibitors, using the method described by Gimbrone, M. A., Cotran, R. S., Leapman, S., and Folkman, J. *J. Natl. Cancer Inst.* 32:413–427 (1974). The cornea provides an avascular matrix into which blood vessels grow and can be quantitated. A total of 116 corneas were implanted as follows: 50 corneas with VX2 carcinoma and empty polymer; 16 with VX2 carcinoma and minocycline polymer; 14 with VX2 carcinoma and heparin/cortisone polymers; and 36 with VX2 carcinoma and cortisone polymers. Five corneas were excluded from the study; three became infected, one lost its polymeric implant, and one was lost when the rabbit died prior to the first reading on day 7.

The corneas were examined with a Zeiss slit lamp stereomicroscope (Carl Zeiss, Inc., Thornwood, N.Y.) on days 7, 14 and 21 after implantation. A total of 111 corneas were evaluated on days 7 and 14, and 77 corneas were assessed on day 21. The angiogenesis response was quantitated by measuring both vessel length and vessel number to provide an angiogenesis index. For vessel length, the span of the blood vessels from the corneo-scleral junction to the leading edge of the new blood vessel front was measured with an ocular microscale eyepiece. The number of blood vessels present was designated, based on the following 4-level scale; 0, 0 vessels; 1, 1–10 vessels; 2, greater than 10 vessels, loosely packed so that details of the iris could be observed through the gaps between the vessels; and 3, greater than 10 vessels, tightly packed so that the iris could not be seen through the gaps between the vessels. An angiogenesis index was then determined as follows:

angiogenesis index=vessel length×vessel density

Histological Examination of Cornea. The rabbits were sacrificed after the last stereomicroscopic examination on day 21 by the i.v. administration of T-61 Euthanasia Solution (Taylor Pharmacal Co., Decatur, Ill.). Representative corneas were removed and placed in phosphate-buffered formalin for 10–14 days, embedded in paraffin, sectioned with a microtome, and stained with hematoxylin and eosin for histological examination.

Statistical Analysis. The angiogenesis indexes for the four groups were compared by using the Kruskai-Wallis test for nonparametric single factor analysis of variance and the Newman-Keuis nonparametric analogue for multiple comparisons, as described by Zar, J. H., *Biostatistical Analysis.* (Prentice-Hall, Inc., Englewood Cliffs, N.J. 1984). Independent analyses were carried out for group values on days 7, 14, and 21.

The results are shown in FIG. 1. Tumor angiogenesis was significantly inhibited ($P<0.05$) by the controlled release of minocycline, cortisone alone, and the combination of heparin and cortisone at 7, 14, and 21 days after implantation. The degrees of inhibition obtained with the three agents were comparable; there were no statistically significant differences among the three inhibitors at any time. Minocycline decreased tumor-induced angiogenesis by a factor of 4.5, 4.4, and 2.9 at 7, 14, and 21 days, respectively. At the end of the experiment, whereas the corneas with empty polymers had large, invasive, exophytic tumors, none of the corneas with minocycline had such vascular masses, as determined by the histological examination. When implanted alone in the cornea, the polymers containing minocycline, cortisone, and the combination of heparin and cortisone did not induce angiogenesis. Polymers containing heparin alone, however, were noted to promote a mild angiogenic response in the cornea.

Histological examination of the corneas with tumor and minocycline-EVAc polymers confirmed the presence of viable tumor adjacent to the polymer, surviving in an avascular state by day 21. Sections of rabbit cornea, prepared and stained with hematoxylin/eosin, showed the extent of tumor growth and neovascularization 21 days after implantation. Examination shows extensive tumor growth and vascularization in the presence of an empty polymer, and minimal tumor burden and vascularization in the presence of minocycline, while the tumor cells adjacent to minocycline-impregnated polymer are viable, although avascular. Thus, despite the prevention of neovascularization through the cornea, the minocycline does not appear to be directly toxic to the tumor cells.

The results confirmed that minocycline, a semisynthetic tetracycline with anticollagenase activity, was an inhibitor of tumor angiogenesis in the rabbit cornea. Minocycline inhibited angiogenesis to an extent comparable to that of the combination of heparin and cortisone. Histological evidence of viable tumor adjacent to the minocycline-EVAc matrix at 21 days suggests that minocycline itself is not directly cytotoxic to mammalian cells. Other data shows that in vitro minocycline significantly prolongs the doubling time of bovine retinal endothelial cells but not C6 glioma, F98 glioma, or 9L gliosarcoma tumor lines.

EXAMPLE 2

Demonstration of Specificity of Minocycline in Inhibiting Endothelial Cells

To test for specificity for inhibiting blood vessel cells, a variety of cells were tested to determine relative sensitivities. One day later increasing doses of minocycline were added, and on the fourth day the cells were counted.

Figure 2A:
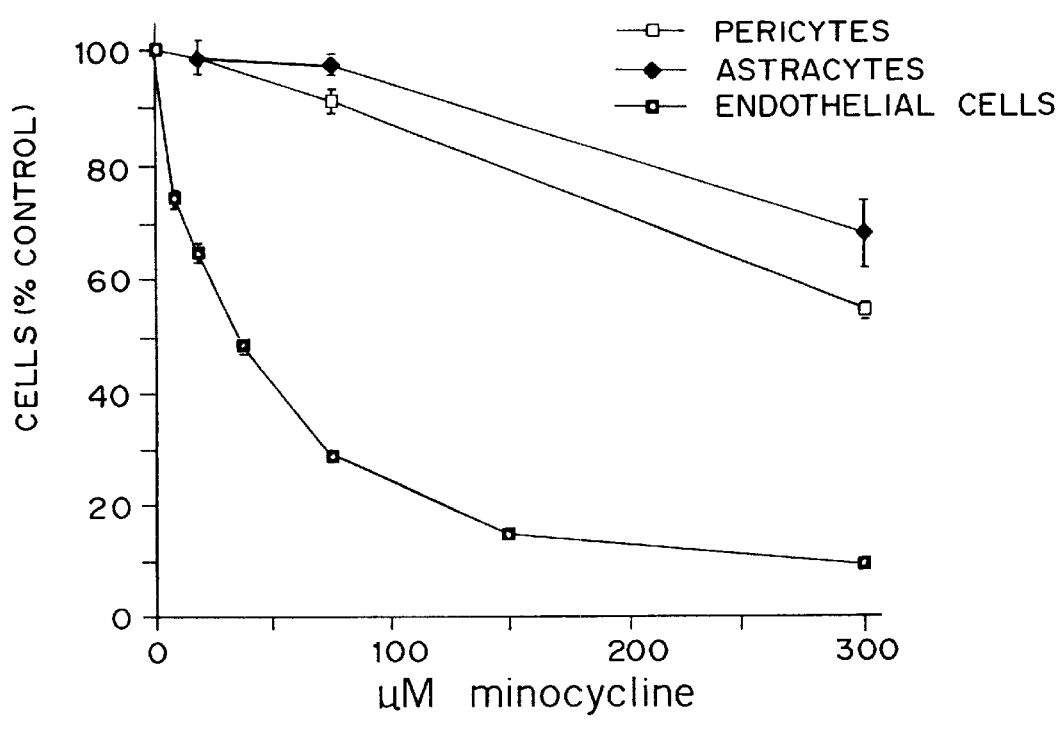

Selective growth inhibition is shown in FIG. 2A where pericytes, astrocytes, and endothelial cells were plated. Only endothelial cell growth was inhibited.

The selective inhibition of DNA synthesis, based on $^3$-H-thymidine uptake, was shown for endothelial cells rather than C6 glioma (brain tumor) cells. The cells were initially plated, and then when nearly confluent, the minocycline was added. Twelve hours later, $^3$H-thymidine was added and six hours later, a TCA precipitation was carried out and the CPM were measured.

The results shown in FIG. 2B demonstrate that the minocycline specifically inhibited DNA synthesis of endothelial cells rather than C6 glioma tumor cells., The minocycline was then tested for effectiveness in inhibiting a variety of endothelial cells. The doubling time of the endothelial cells was measured in the presence of the minocycline.

The results shown in FIG. 2C show that both paraaortic endothelial cell growth and bovine retinal endothelial cell growth were inhibited by minocycline.

Modifications and variations of the compositions of the present invention, and methods for use, will be obvious to those skilled in the art from the foregoing detailed description. Such modifications and variations are intended to fall within the scope of the appended claims.

We claim:

1. A method for inhibiting angiogenesis and capillary endothelial cell proliferation in a patient suffering from a hyperproliferative disorder comprising
administering an effective amount of a tetracycline having anti-collagenase activity in a biocompatible polymeric delivery device to the site where the angiogenesis and endothelial cell-proliferation is to be inhibited, wherein the tetracycline is administered in a dosage effective to inhibit angiogenesis and inhibit capillary endothelial cell proliferation, and the dosage is greater than an antibacterially effective amount of the tetracycline.

2. The method of claim 1 wherein the tetracycline is administered in a dosage of between one and 500 micromolar.

3. The method of claim 1 further comprising administering the tetracycline in a pharmaceutical vehicle suitable for topical application to the skin.

4. The method of claim 1 wherein the biocompatible polymeric delivery device is implanted at the site where angiogenesis is to be inhibited.

5. The method of claim 1 further comprising providing the tetracycline in a pharmaceutical vehicle suitable for injection or infusion.

6. The method of claim 1 wherein the tetracycline is administered systemically.

7. The method of claim 1, wherein the tetracycline is administered at the site of a tumor, wherein the effective dose is a dose effective in diminishing the number of blood vessels growing into the tumor.

8. The method of claim 1, wherein the tetracycline is administered to an eye, wherein the effective dose is a dose effective in diminishing the symptoms of eye disease characterized by abnormal neovascularization.

9. The method of claim 1 wherein the tetracycline is minocycline.

10. The method of claim 1 wherein the tetracycline does not have antibacterial activity.

11. The method of claim 1 wherein the tetracycline is formulated in a formulation selected from the consisting of ointments, creams, gel, pastes, foams, aerosols, suppositories, pads, and gelled sticks.

12. The method of claim 1 wherein the biocompatible polymeric delivery is formed of polymer selected from the group consisting of polyanhydrides, polyorthoesters, polyglycolic acid, polylactic acid, polyethylene vinyl acetate, ethylene vinyl acetate, and copolymers and blends thereof.

13. The method of claim 1 wherein the tetracycline is in a formulation further comprising a compound selected from the group consisting of preservatives, antioxidants, immunosuppressants, and cytotoxic agents.

* * * * *